US004001775B2

United States Statutory Invention Registration [19]

[11] Reg. Number: H1775

Ligler et al. [45] Published: Jan. 5, 1999

[54] RAPID ASSAY FOR DETECTION OF ENDOTOXINS

[76] Inventors: Frances S. Ligler, 12400 Beall Mountain Rd., Potomac, Md. 20854; Elizabeth A. James, 7910 Edinburgh Dr., Springfield, Va. 22153

[21] Appl. No.: 422,103

[22] Filed: Apr. 14, 1995

Related U.S. Application Data

[63] Continuation-in-part of Ser. No. 102,933, Aug. 6, 1993, Pat. No. 5,496,700.

[51] Int. Cl.[6] ..... G01H 33/554

[52] U.S. Cl. ..... 435/7.32; 435/7.92; 435/7.93; 436/518

[58] Field of Search ..... 435/7.32, 7.92, 435/7.93; 436/518

[56] References Cited

U.S. PATENT DOCUMENTS

| | | | |
|---|---|---|---|
| 4,576,912 | 3/1986 | Yaverbaum et al. | 435/7 |
| 4,671,938 | 6/1987 | Cook | 422/57 |
| 4,808,314 | 2/1989 | Karplus et al. | 210/638 |
| 4,844,869 | 7/1989 | Glass | 422/52 |
| 4,870,158 | 9/1989 | Karol et al. | 530/319 |
| 4,906,567 | 3/1990 | Connelly | 435/7 |
| 5,057,598 | 10/1991 | Pollack et al. | 530/387 |
| 5,077,210 | 12/1991 | Ligler et al. | 435/176 |
| 5,093,235 | 3/1992 | Williams et al. | 435/7.32 |
| 5,175,089 | 12/1992 | Fine et al. | 435/23 |
| 5,179,018 | 1/1993 | Bogard, Jr. et al. | 530/388.15 |
| 5,198,339 | 3/1993 | Hansen et al. | 435/7.2 |
| 5,316,911 | 5/1994 | Back et al. | 435/7.9 |
| 5,356,778 | 10/1994 | Hansen et al. | 435/7.2 |

FOREIGN PATENT DOCUMENTS 0265127 4/1988 European Pat. Off. .

OTHER PUBLICATIONS

Levin et al., "Clottable Protein in Limulus: Its Localization and Kinetics of Its Coagulation by Endotoxin", pp. 186–197.

Minobe et al., "Specific Assay for Endotoxin Using Immobilized Histidine and Limulus Amebocyte Lysate", Analytical Biochemistry, 198, pp. 292–297 (1991).

Mertsola, et al., "Detection of Experimental *Haemophilus Influenzae* Type b Bacteremia and Endotoxemia by Means of an Immunolimulus Assay", Journal of Infectious Diseases pp. 353–358, No. 164 (1991).

Mertsola et al., Specific Detection of Haemophilus Influenza Type b Lipooligosaccharide by Immunoassay, Journal of Clinical Microbiology, pp. 2700–2706, vol. 28, No. 12, Dec. (1990).

Lim, "A One–Step Two Particle Latex Immunoassay for the Detection of Salmonella Typhi Endotoxin", Journal of Immunological Methods, pp. 257–261, No. 135 (1990).

Mujumdar et al., "Cyanine Dye Labeling Reagents: Sulfoindocyanine Succinimidyl Esters", Bioconjugate Chemistry, vol. 4, No. 2, Mar./Apr. 1993.

(List continued on next page.)

*Primary Examiner*—Peter A. Nelson

[57] ABSTRACT

The presently claimed invention is an apparatus and method for the detection of endotoxin via a competitive assay.

2 Claims, 5 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OTHER PUBLICATIONS

Ogert, et al., "Detection Clostridium Botulinum Toxin A Using A Fiber Optic–Based Biosensor", Analytical Biochemistry 205, pp. 306–312 (1992).

Shriver–Lake, et al., "The Effect of Tapering the Optical Fiber on Evanescent Wave Measurements", Analytical Letters, 25(7), pp. 1183–1199 (1992).

Golden, et al., "Flurometer and Tapered Fiber Optic Probes fro Sensing in the Evanescent Wave", Optical Engineering, pp. 1458–1462, Jul. 1992.

Anderson, et al., "A Fiber Optic Biosensor: Combination Tapered Fibers Designed for Improved Signal Acquisition", Biosensors and Bioelectronics 8, pp. 249–256 (1993).

Bhatia, et al., "Use of Thiol–Terminal Silanes and Heterobifunctional Crosslinkers for Immobilization of Anitbodies on Silica Surfaces", Analytical Biochemistry 178, pp. 408–413 (1989).

Oellerich, M., *J. Clin. Chem. Clin. Biochem.*, vol. 22, pp. 895–904, 1984.

Mertsola, et al., *J. Immunol. Methods*, vol. 122, No. 2, pp. 219–226, 1989 (abstract only).

RAPID ASSAY FOR DETECTION OF ENDOTOXINS

CROSS REFERENCE TO RELATED APPLICATION

This application is a continuation-in-part of parent patent application entitled OPTICAL IMMUNOASSAY FOR MICROBIAL ANALYTES USING NON-SPECIFIC DYES of Frances S. Ligler et al. designated by Ser. No. 08/102,933 and Navy Case No. 75,315 and filed in the U.S. Patent and Trademark Office on Aug. 6, 1993now U.S. Pat. No. 5,496,700, which parent application is still pending before the U.S. Patent and Trademark Office, and which patent application is incorporated herein by reference in its entirety and for all purposes.

BACKGROUND OF THE INVENTION

1. Field of the Invention

The present invention relates to an apparatus and method for detecting endotoxin.

2. Description of the Related Art

All gram-negative bacteria and many fungi have endotoxin as a major constituent of their cell surface. Most gram-positive bacteria have a similar, endotoxin-like molecule as a constituent of the cell surface. In general, bacterial endotoxins partially consist of a highly variable outer region and a conserved inner core. The variable outer region is composed of repeating oligosaccharide (sugar) units comprising the O-ANTIGENIC region. The OUTER CORE and the O-ANTIGEN region, found within the cell walls of various gram negative bacterial species, show species differentiation among endotoxins. Bacterial endotoxins also consist of a relatively constant, conserved inner core region. The conserved inner core consists of the KDO region and the heptose region. The lipid A moiety (also a conserved portion of the endotoxin) is the toxic region of the endotoxin found in the cell surface of gram-negative bacteria. An exemplary endotoxin is shown below:

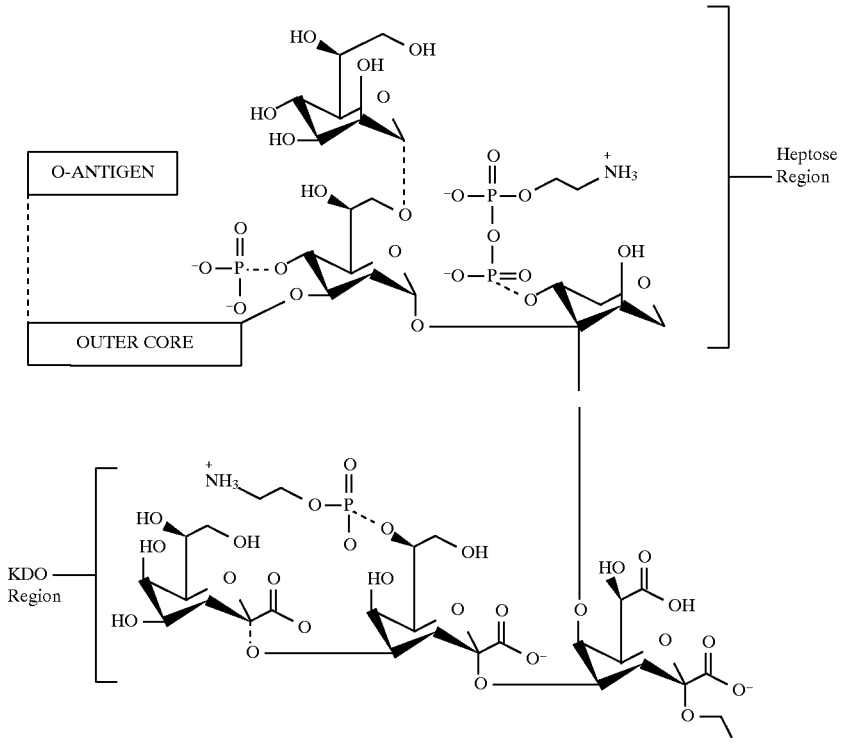

-continued

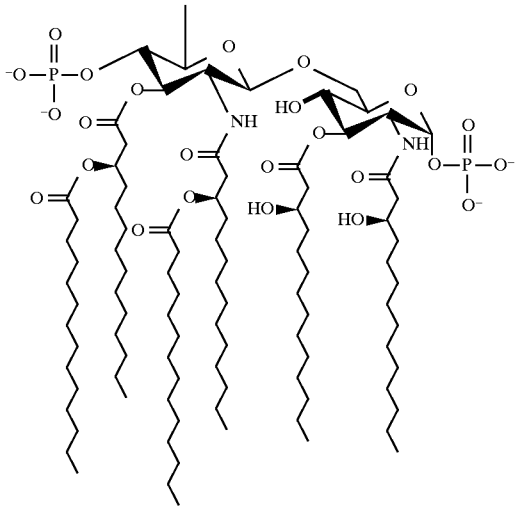

Endotoxin is an extremely powerful stimulator of the immune system. The devastating effects of bacterial infections and septicemia are in large part due to endotoxin. Mortality rates, due to septicemia are high, 60% or more. The most effective treatment of endotoxin related problems is early detection in real time with high sensitivity. Additionally, endotoxin is a significant contaminant in food products and pharmaceutical products. Accurate determination of endotoxin concentration is required prior to product distribution. To satisfy the requirements of industrial production, endotoxin assays must be accurate, rapid and cost effective.

Levin and Bang observed in the horseshoe crab (Limulus polyphemus) that blood coagulation was a consequence of gram-negative bacterial infections. See Levin, J., Bang, F.B., 19 THROMBOS. DIATH. HAEMORRH., 186–197 (1968), incorporated by reference herein in its entirety and for all purposes. When an extract of the horseshoe crab blood was prepared and tested, a gelation reaction was observed in the presence of endotoxin. Levin and Bang postulated that endotoxin mediated the gelation reaction of horseshoe crab blood. They further postulated that the gelation reaction was initiated enzymatically. The enzyme responsible for initiating the gelation reaction was identified as limulus amebocyte lysate (LAL).

The reaction mechanism for the gelation reaction in horseshoe crab blood involves the activation of a proclotting enzyme by $Ca^{+}$and endotoxin. The activated proclotting enzyme catalyzes the hydrolytic cleavage of coagulogen (a clottable protein of 215 amino acid residues) into polypeptide subunits. Clotting occurs following the cleavage of the 215 amino acid coagulogen protein into a soluble peptide of 45 amino acid residues and an insoluble peptide (coagulin) of approximately 170 amino acid residues. The insoluble 170 amino acid peptide, coagulin, undergoes polymerization to form a stable clot or gel. The presence of a gel or clot indicates the presence of endotoxin. The formation of a gel or clot is used in what is known as the limulus amebocyte lysate method (LAL). The LAL method and its variations are the most commonly used endotoxin detection methods.

The standard LAL tests are of two types, gelation and chromogenic. Both assays are based on the enzyme cleavage reaction of coagulogen, but, in the chromogenic assay, a color is produced during the cleavage step. Thus, the presence of the color instead of a clot or gel indicates the presence of endotoxin.

The limitations of these LAL assays include limitations of specificity, limitations of interfering substances and limitations of reproducibility. The LAL techniques require an enzymatic reaction to detect the presence of endotoxin. Hence, substances that inhibit or stimulate enzymatic cleavage of the 215 amino acid coagulogen protein will lead to false-negative or false-positive results, respectively. In samples, such as serum or blood, there are several factors known to interfere with the LAL method. For example, the LAL enzyme cascade is inhibited by antibiotics, hormones, heavy metals, amino acids, alkaloids, carbohydrates, plasma proteins, enzymes, electrolytes and B-1,3-D-glucan. See Satoshi, M., Masahiro, N., Taizo, W., Tadashi, S. and Tetsuya, T., 198 ANALYTICAL BIOCHEMISTRY 292–297 (1983), incorporated by reference herein in its entirety and for all purposes. For example, false positive gelation can be caused by thrombin, thromboplastin, RNA, RNAase, trypsin, trypsin-like enzymes, lipotechoic acid and peptidoglycan fragments. False negative results (blocking gelation) can be caused by trypsin inhibitors, EDTA, other calcium binding reagents, high salt concentrations and semi-synthetic penicillins. See European Patent No. EP 0 265 127 A1, incorporated herein by reference in its entirety and for all purposes.

Another detection strategy is the sandwich enzyme linked immunosorbent assay (ELISA). This assay (ELISA) involves immobilizing an antibody specific for a conserved region of the endotoxin (e.g. the KDO region). Using ELISA, the endotoxin immobilized (i.e. captured) by a first antibody is detected by using a second antibody attached to another antigenic site of the endotoxin and a chromogenic enzyme. The sensitivity of this technique is about 1 $\mu$g/ml. This test is time consuming, requiring over 4 hours.

There are several limitations of the ELISA assay used in the detection of endotoxin. Endotoxin has low affinity for ELISA plates. The lack of endotoxin affinity diminishes sensitivity. When a first antibody is immobilized onto an ELISA plate and endotoxin is bound by (i.e. captured by or immobilized by) the first antibody, there appears to be significant interference with the binding of a secondary antibody to the immobilized endotoxin, used in the detection of endotoxin. Finally, the sensitivity of ELISA assays (in the 1μg/ml range) is far below that of the LAL assays (1 ng/ml for chromogenic LAL assay) and higher than clinically relevant concentrations of endotoxin of about 1 ng/ml.

Other variations of the LAL assays have been developed. These involve combining the LAL assay with an enzyme linked immunosorbent assay (ELISA). A capture antibody (i.e. a polyclonal first anti-endotoxin antibody) for the oligosaccharide region of an endotoxin is immobilized on a microtiter plate. Endotoxin is introduced over the ELISA microtiter plate. The bound endotoxin is detected by using the chromogenic LAL system. Sensitivity is in the range of 2 pg/ml in PBS and 10 pg/ml in diluted plasma. See Mertsola, J., Cope, L.D., Munford R.S., McCracken, G.H. and Hansen, E.J, *Detection of Experimnental Haemophilus influenzae Type b Bacteremia and Endotoxemia by Means of an Immunolimulus Assay,* 164 THE JOURNAL OF INFECTUOUS DISEASES 353–358 (1991), incorporated by reference herein in its entirety and for all purposes. See Mertsola et al., *Specific Detection of Haemophilus influenzae Type b Lipooligosaccharide by Immunoassay,* 28 (12) JOURNAL OF CLINICAL MICROBIOLOGY pp. 2700–2706 (December 1990), incorporated by reference herein in its entirety and for all purposes. The combination ELISA/LAL assay requires at least 12–24 hours to complete.

In the combination ELISA/LAL assay systems, the limitations are cumulative. The endotoxin is first bound to an ELISA microtiter plate via a reaction with an antibody or other capture molecule and the endotoxin is then detected using the chromogenic LAL assay. The substances that interfere with the LAL assay also interfere with the combination ELISA/LAL assay. In addition, the LAL reaction portion of the assay requires a minimum of 40 minutes to 2 hours to perform and requires that serum be removed prior to the addition of the enzyme because serum components may inhibit the enzyme activity. the LAL assay does not reliably quantitate the amount of endotoxin present. Detection of endotoxin in serum is five times (5x) less sensitive than detection of endotoxin in buffer.

An antibody-based test reported to have higher sensitivity than ELISA is the latex immunoassay technique. In this assay, latex beads are coated with a monoclonal antibody (Ab1) specific for the O-9 determinant of endotoxin. The beads are then incubated with a solution containing lipopolysaccharide (LPS; synonym for endotoxin). A magnetic bead coated with another monoclonal antibody (Ab2) specific for a different antigenic site of an endotoxin is added to the LPS solution surrounding the latex beads coated with Ab1. In the presence of LPS, the magnetic beads (coated with Ab2) complex with the latex beads (coated with Abl), via the LPS, and the latex beads are sedimented by the use of a magnet. The quantitation of LPS is based on the turbidity of the solution remaining after sedimentation of the magnetic beads (i.e. measuring the latex beads still remaining in solution after sedimentation). The sensitivity varies based on incubation time from 5–30 minutes. Sensitivities of 0.9–25 ng/ml were reported. A serious disadvantage of this assay is that it is inhibited by serum and by high concentrations of endotoxin. See Lim, P., 135 JOURNAL OF IMMUNOLOGICAL METHODS 257–261 (1990), incorporated by reference herein in its entirety and for all purposes.

U.S. Pat. No. 5,057,598 (Pollack et al.) discloses the use of monoclonal antibodies for the immunological detection of endotoxin or endotoxin bearing organisms. See Pollack et al. (U.S. Pat. No. 5,057,598), incorporated by reference herein in its entirety and for all purposes. Pollack et al. states, at column 18, lines 24–28, that detection of endotoxin can be carried out in hours compared with detection of endotoxin based on standard microbiological or cultural methods in days. Clearly, a detection method that works in a time shorter than hours would be advantageous.

The oldest and best known test for endotoxin is the rabbit pyrogen test. This assay has a low sensitivity, is expensive and is plagued with reproducibility problems since different rabbits have different sensitivities to endotoxin challenge. Additionally, animal tests are very time consuming and, therefore, of limited application in a clinical setting.

The immunoassays for endotoxin previously described are all sandwich immunoassays which include the binding of two proteins to the endotoxin molecule. In general, sandwich assays are the preferred approach for the detection of large molecule, whereas competition assays are used for the detection of small molecules with only a single protein binding site. Another sandwich assay for endotoxin, reported by Connelly, uses lipopolysaccharide binding proteins of amebocyte lysates and labelled detection reagents. See U.S. Pat. No. 4,906,567, incorporated herein by reference in its entirety and for all purposes. The general scheme used by Connelly involves holding lipopolysaccharide binding proteins from one or more various organisms (See Col. 4, lines 62–68, U.S. Pat. No. 4,986,567 of Connelly) within the wells of microtiter plates for about 2 hours followed by washing in PBS (phosphate buffered saline), followed by holding BSA (bovine serum albumin) within the same microtiter plate wells for about 1 hour, followed by introduction of an endotoxin containing sample (or sample suspected of containing endotoxin) and holding the sample for about 30 minutes to about 1 hour within the same wells, followed by introduction of a horseradish peroxidase conjugated to an LPS antibody via the heterobifunctional linking agent N-succinimidyl-4-(N-maleimidomehtyl) cyclohexane-1-carboxylate (SMCC) and holding the LPS antibody-peroxidase conjugate within the same wells for for about 30–60 minutes, followed by washing in PBS and introducing a chromogenic substrate, tetramethylbenzidine (TMB) into the same wells and holding for about another 10–15 minutes before taking an optical density measurment at 630 nm. See Connelly at Examples 1, 2, 3, 4 and 5. Id.

In all of the Connelly examples, the pH is maintained at 9.0 or less and the time to reading the optical density (OD) from the time when the sample containing LPS (or suspected of containing LPS) is first intrtoduced into the microtiter plate wells is between about 1 1/6 hours (1 hour, 10 min.—simultaneous or staggered addition of example 5 of Connelly at Col 12, lines 15–35) to about 3 1/6 hours (3 hours, 10 min.--sequential addition of example 4 of Connelly at Cols. 10 and 11).

European Patent (EP 0 265 127) of Harvey and Wilson describes a method and apparatus for the detection of endotoxin using either polymyxin, an octapeptin, or other similar cyclic peptides. An assay is carried out wherein the amount of a polymyxin-endotoxin conjugate (hereinafter, polymyxin B-LPS conjugate) formed is quantitated. The amount of the polymyxin B-LPS conjugate formed is quantitated by attaching a label to either the polymyxin B or to the endotoxin. The labelled polymyxin B-LPS conjugate is then measured. At page 7, lines 27–31 of EP 0 265 127 it is stated that:

> In one form of the assay, the analyte which contains LPS and a standard, labelled, LPS preparation compete for a limited amount of immobilized polymyxin B, and the amount of label bound to the polymyxin B is then quantitated. (Emphasis added.) From the above quoted language, it appears at first glance that the analyte (containing LPS or suspected of containing LPS) and the standard, labelled, LPS preparation are simultaneously placed in proximity to the immobilized polymyxin B wherein the analyte LPS and the standard, labelled LPS compete for binding to the polymyxin B. However, upon closer examination of Examples 1, 2, 3, and 4 of EP 0 265 127, it appears that the analyte LPS and the standard, labelled, LPS preparation are not added simultaneously. Instead, the analyte LPS and the standard, labelled, LPS preparation are added consecutively in proximity to the exemplary immobilized polymyxin B. The requirement that the sample and labelled reagent be added sequentially causes the assay to be inherently slower than an assay involving simultaneous addition of analyte and labelled endotoxin. Examples 1–4 describe slow, multistep reactions.

Example 1 of EP 0 265 127 describes a process wherein the following steps are executed:

(1) binding capacity of immobilized polymyxin B for LPS is determined by using isotopically labelled LPS ($^{14}$C LPS);

(2) incubating test analyte solution (containing LPS or suspected of containing LPS) with immobilized polymyxin B;

(3) adding a known quantity of isotopically labelled LPS ($^{14}$C LPS) to the mixture of step (2);

(4) measuring the amount of isotopically labelled LPS in solution;

(5) subtracting the amount of isotopically labelled LPS in solution (i.e. unbound isotopically labelled LPS) from the total amount of $^{14}$C LPS introduced in step (3) to determine the amound of $^{14}$C LPS bound to the immobilized polymyxin B; and (6) subtracting the amount of $^{14}$C LPS bound to the immobilized polymyxin B determined in step (5) from the binding capacity of the immobilized polymyxin B in step (1) to determine the amount of analyte LPS present. The net result of step (6) indicates the amount of analyte LPS present and bound to the immobilized polymyxin B.

Example 2 of EP 0 265 127 describes a process wherein the following steps are executed:

(1) incubating analyte LPS samples with a known quantity of polymyxin B alkaline phospatase conjugate in sufficient excess to promote binding between all the analyte LPS and the polymyxin B-alkaline phosphatase conjugate;

(2) incubating the mixture of step (2) with an immobilized, standard LPS preparation to bind the unbound excess of the polymyxin B alkaline phosphatase conjugate from step (1);

(3) rinsing the preparation of step (2);

(4) measuring the amount of the excess polymyxin B-alkaline phosphatase conjugate of step (1) now bound to the immobilized, standard LPS preparation of step (2); and (5) subtracting the amount of excess polymyxin B alkaline phosphatase determined in step (4) from the total polymyxin B alkaline phosphatase conjugate used in step (1) to determine the amount of analyte LPS present. An assay time of 1 hour plus the time necessary for scintillation counting was required. Sensitivity was 10 $\mu$g/ml. The statement was made that increasing the specific activity of the $^{14}$C-LPS would increase sensitivity of the assay. However, increasing specific activity also increases bacground so that the gain from such an improvement in the labelled reagent is rarely greater than a factor of 10. In addition, radiolabels may be hazardous to an inexperienced user and involve undesirable problems of disposal as hazardous waste.

Example 3 of EP 0 265 127 describes a process wherein the following steps are executed:

(1) incubating a limited excess amount of immobilized polymyxin B with analyte LPS to bind all analyte LPS;

(2) incubating an excess of standard, LPS-alkaline phosphatase conjugate with the mixture of step (1) and removing excess standard LPs-alkaline phosphatase by rinsing;

(3) measuring the amount of standard LPS-alkaline phosphatase conjugate bound in step (2) to the immobilized polymyxin B; and (4) subtracting the amount of the immobilized LPS-alkaline phosphatase conjugate bound in step (2) from the total amount of immobilized polymyxin B to determine the amount of analyte LPS bound in step (1). It is difficult to imagine how Example 3 is characterized as a "displacement ELISA" (see p. 10, line 21) since it is stated at p. 8, line 25 that LPS can block the binding of $^{14}$C LPS to polymyxin B/S4B. See EP 0 265 127.

Example 4 of EP 0 265 127 describes a process wherein the following steps are executed:

(1) immobilizing analyte LPS and rinsing;

(2) binding polymyxin B-alkaline phosphatase conjugate to immobilized analyte LPS of step (1); and (3) measuring the amount of labelled polymyxin B attached to the immobilized analyte LPS of step (1) to determine the amount of analyte LPS present in an analyte sample.

Examples 2–4 provide neither data nor experimental details. ELISA assays are generally less sensitive than radioimmunoassays using the same reagents and same general approach. Thus, the approaches described in examples 2–4 would not be expected to produce sensitivity greater than about 10 $\mu$g/ml. The use of enzymes as labels also involve problems of interferents from the sample matrix, increasing background response over time during the assay, and increasing instability of the enzyme label during storage.

In all of the assay formats described, European Patent (EP 0 265 127) has several drawbacks:

(1) washing steps are required in Examples 2, 3, and 4;

(2) lengthy incubation steps are required in Examples 1, 2, 3, and 4, so that all assays require more than 1 hour to perform;

(3) a radioactive label is used in example 1;

(4) enzyme labelled LPS or enzyme labelled polymyxin B is used in Examples 2, 3, and 4; and (5) analyte samples used are extracts from, for example, body fluids (see p. 7, line 33 of EP 0 265 127). (6) no evidence of sensitivity or potential sensitivity greater than $\mu$g/ml is provided.

Thus, there remains a need for an endotoxin assay with high sensitivity to concentrations as low as about 1 ng/ml which can be used in non-homogeneous samples such as serum or saliva, which has no requirement for enzymes or radiolabels, which requires very little manipulation by the operator, which is rapid, which can be used with intact cells, cell fragments or solubilized cells, which can be used on a wide variety of clinical and environmental samples, which requires minimal or no sample preparation, which can be used in a wide variety of environments, structural forms and conditions, which can be used rapidly (between about 15 seconds to about 10 minutes) to test for the presence of endotoxin and which can be adapted to determine the specific type of endotoxin detected.

SUMMARY OF THE INVENTION

It is, therefore, an object of this invention to provide a rapid test for endotoxin.

It is another object of this invention to provide a rapid test for endotoxin which can be performed in the presence of serum or other biological samples including, but not limited to, urine, saliva, and mucus.

It is yet another object of this invention to provide a test for endotoxin which has no requirement for enzymes.

It is a further object of this invention to provide an assay requiring very little manipulation by the operator.

It is yet a further object of this invention to provide a rapid test for endotoxin which is sensitive to quantities as low as 1 ng/ml.

It is even a further object of this invention to provide a rapid test for endotoxin in intact cells, cell fragments or purified endotoxin.

It is an additional object of this invention to provide a rapid test for endotoxin in aqueous samples, for example, from the environment or manufacturing processes.

It is an additional object of this invention to provide a rapid test for endotoxin in a wide variety of environments, structural forms and conditions.

It is an additional object of this invention to provide a rapid test for endotoxin and, if desired, to diagnose the specific type of endotoxin detected.

These and other objects of the presently claimed invention are accomplished by a process which is fast, sensitive, requires no enzyme linked detection systems and can be performed successfully with non-homogeneous samples containing endotoxin. The claimed assay relies on the binding of an endotoxin to a suitable capture molecule and the competitive detection of the capture molecule-endotoxin complex without the use of enzymatic reactions to visualize or enhance detection. For example, a fluorescent dye may be used to label the capture-molecule endotoxin complex and form an exemplary capture molecule-endotoxin-fluorescent label complex. Detection of the exemplary fluorescent label may be carried out by detecting a fluorescence signal obtained from the evanescent wave region of a fiber optic waveguide probe wherein the capture molecule-endotoxin-label complex is immobilized on the surface of the sensing portion of the fiber optic waveguide probe.

DETAILED DESCRIPTION OF THE DRAWINGS

Figure 4:
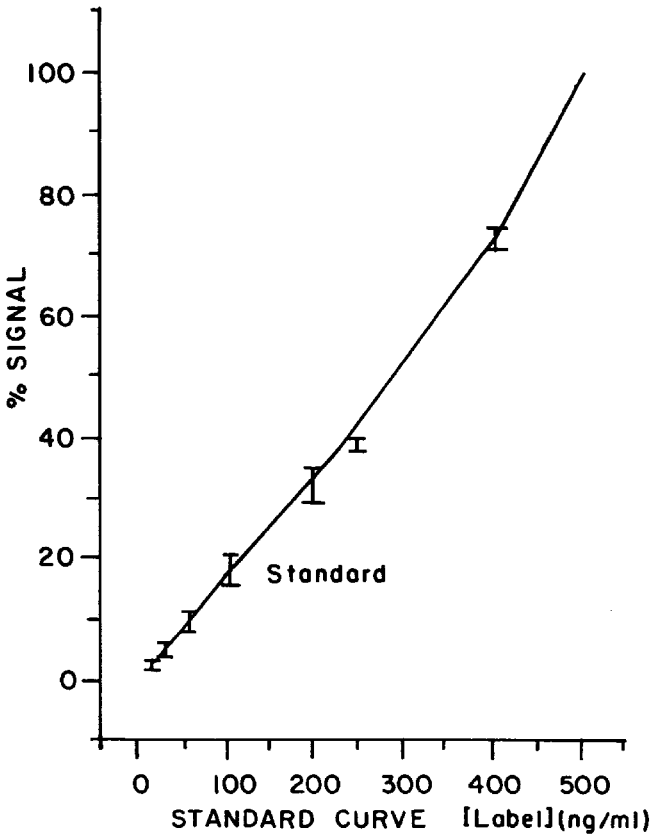

FIG. 4 is a concentration-response curve obtained from the binding of increasing concentrations of fluorescently labelled *E. coli* 0128:bl2 endotoxin to a capture molecule, polymyxin B, the capture molecule being immobilized on to the surface of a combination tapered fiber optic waveguide probe. The response is measured in microvolts ($\mu$Volts) which response varies proportionately with the concentration of endotoxin present in the sample tested.

Figure 5:
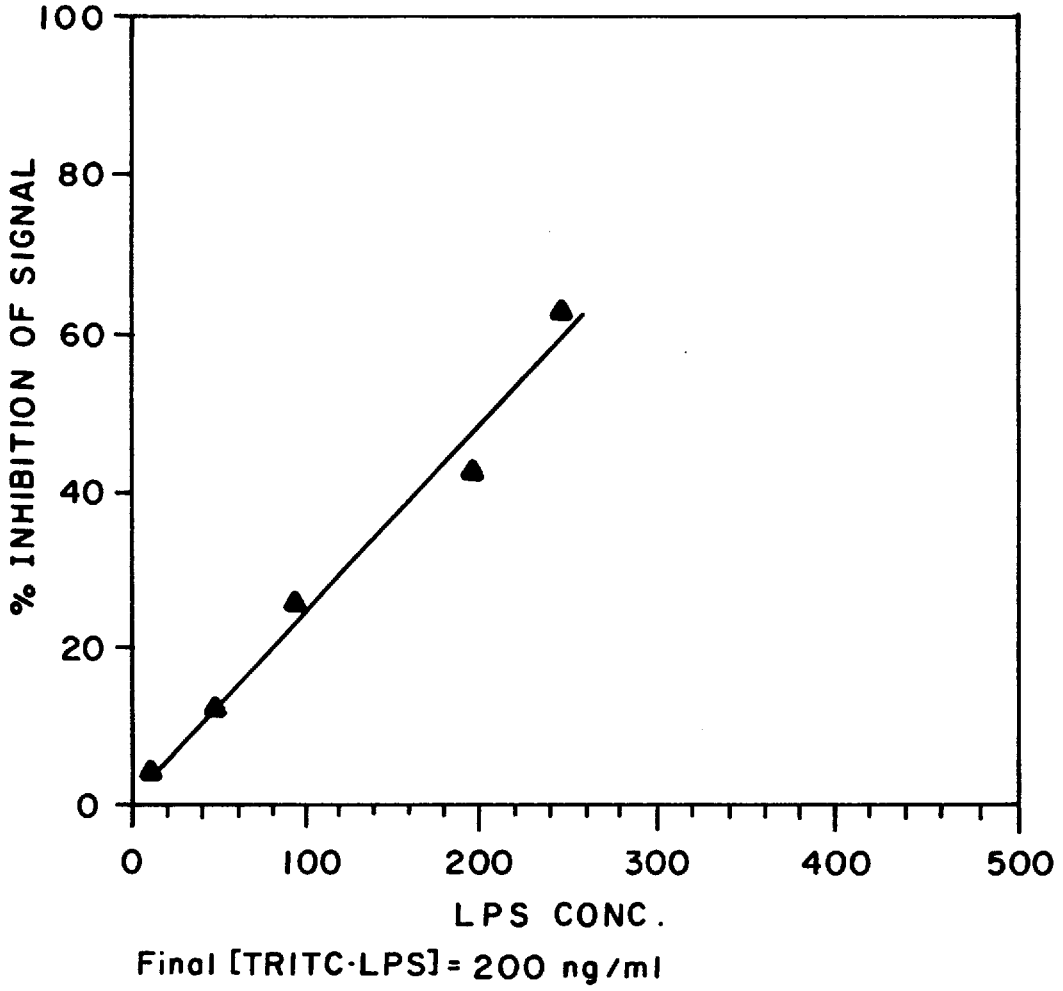
Figure 6:
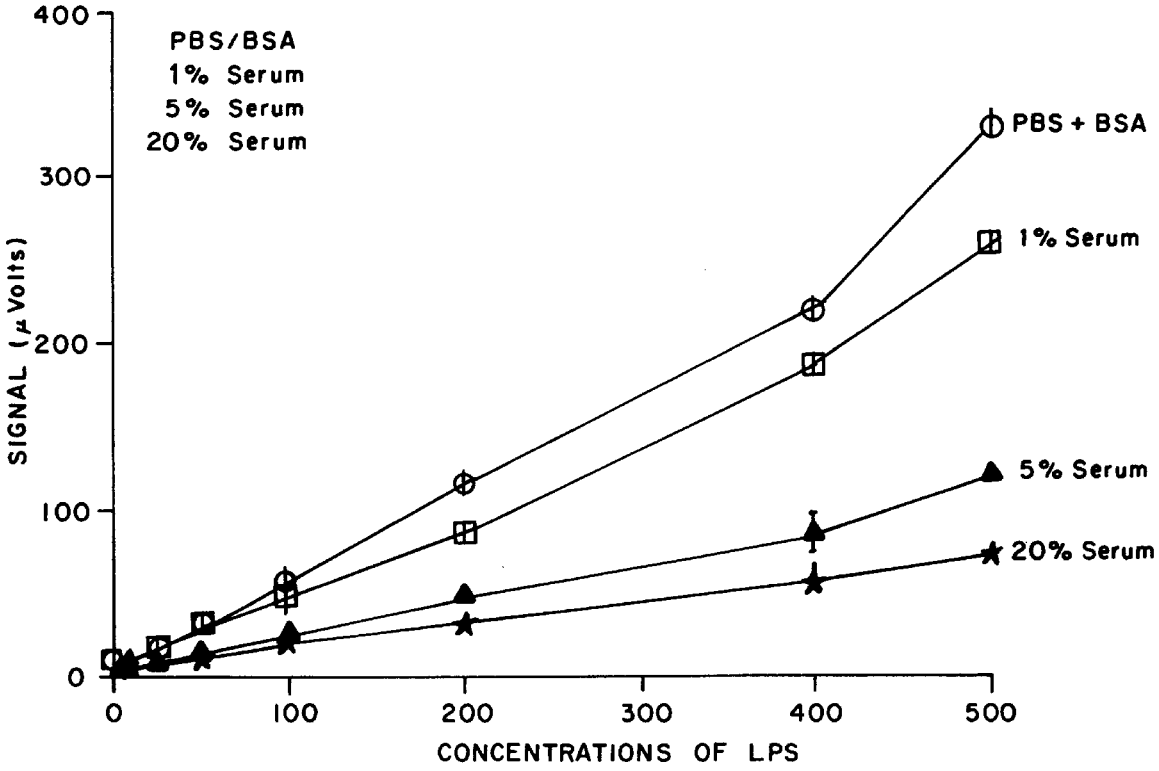

FIG. 5 is a concentration-response curve obtained from the competitive binding of increasing concentrations of unlabelled *E. coli* 0128:bl2 endotoxin in the presence of fluorescently labelled *E. coli* 0128:bl2 endotoxin. The capture molecule was polymyxin B FIG. 6 is a concentration response curve obtained from the binding of increasing concentrations of fluorescently labelled *E. coli* 0128:bl2 endotoxin to a capture molecule, polymyxin B, the capture molecule being immobilized on to the surface of a fiber optic waveguide. The response is measured in microvolts ($\mu$Volts) which response varies proportionately with the concentration of endotoxin present in the sample tested and each point is an average of triplicate determinations.

Figure 7:
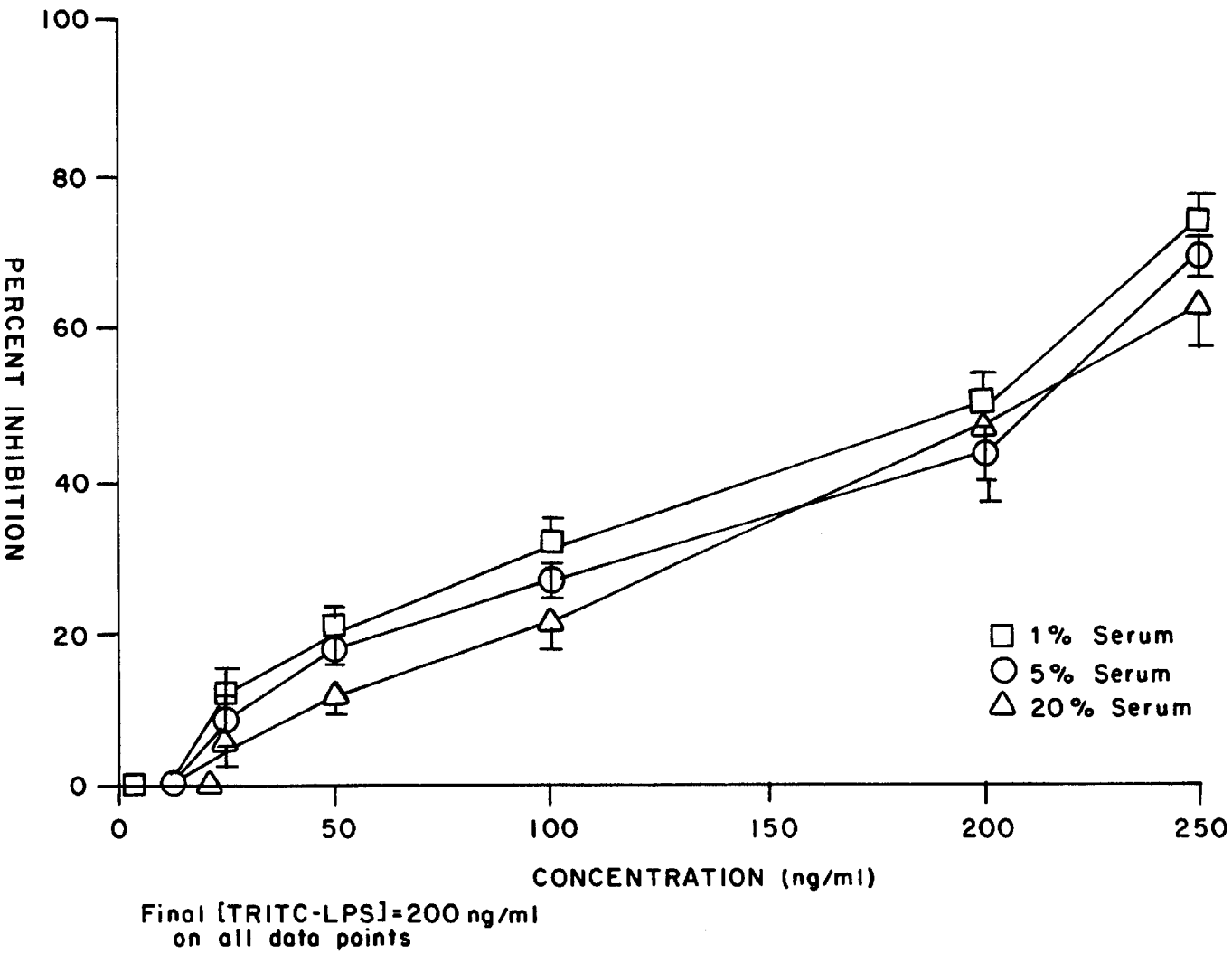

FIG. 7 is a concentration-response curve obtained from the competitive binding of increasing concentrations of unlabelled *E. coli* 0128:bl2 endotoxin in the presence of fluorescently labelled *E. coli* 0128:bl2 endotoxin. The capture molecule was polymyxin B.

DETAILED DESCRIPTON OF THE PREFERRED EMBODIMENTS

The following detailed description of the invention is provided to aid those skilled in the art in practicing the present invention. However, the following detailed description of the invention should not be construed to unduly limit the present invention. Variations and modifications in the embodiments discussed may be made by those of ordinary skill in the art without departing from the scope of the present inventive discovery.

Broadly, the competetive assay of the presently claimed invention comprises:

(1) one or more endotoxin capture molecules immobilized upon a substrate;

(2) a standard sample of one or more labelled endotoxin molecules;

(3) a means for detecting the presence of one or more endotoxin capture molecule-labelled endotoxin molecule complexes (ECM-LEM complexes), said one or more ECM-LEM complexes forming in the presence of one or more unlabelled analyte endotoxin molecules (AEM); and (4) a means for measuring the quantity of ECM-LEM complexes formed.

The capture molecules include but are not limited to antibodies, lectins, cell receptors, antibiotics, endotoxin binding proteins, or specifically engineered peptides referenced in Random Peptide Libraries: A Source of Specific Protein Binding Molecules by J.J. Devlin et al., published in SCIENCE, Vol. 24, pp. 404–405 (1990), incorporated herein by reference in its entirety and for all purposes. Antibodies and antibiotics (such as polymyxin B) may be preferred simply because of their specificity, availability and stability following immobilization.

The capture molecule can be adsorbed or covalently bound to the substrate. Procedures for immobilizing capture molecules onto a substrate (e.g. solid surface) are given in U.S. Pat. No. 5,077,210 of Ligler et al., incorporated herein by reference in its entirety and for all purposes.

Exemplary capture molecules, such as antibiotics, lectins, antibodies, and endotoxin binding proteins, are covalently immobilized on a substrate carrying exemplary surface reactive groups such as hydroxyl groups. Exemplary substrates (e.g. solid supports) have or can be modified to have surface reactive groups such as hydroxyl groups which can be reacted with a capture molecule for direct crosslinking or with a silane or alkyl thiol film for indirect crosslinking. The substrate onto which the capture molecule is immobilized depends only on the type of system used to quantify the amount of unlabelled analyte endotoxin molecules present. Exemplary substrates may include slides, beads (magnetic, synthetic or natural polymers), optical fibers, metal films, and cuvettes (quartz, glass, silica). The exemplary surface of the substrate may be smooth, flat, curved, round, rough, or with or without edges. Suitable substrates are preferably inorganic substrates including but not limited to silicon, glass, silica, quartz, metal oxides, organic polymers, and the like which can be for example optical fibers, wires, wafers, films, discs or planar surface, microscope slides, or beads. Generally, the solid surfaces (substrates) have or can be modified to have functional groups such as surface hydroxyl groups that react with exemplary silanizing reagents or exemplary metal oxide groups reactive with exemplary alkyl thiol reagents.

Endotoxin has several chemically reactive groups including primary amines and carboxyl groups. Such amine and carboxyl groups allow for label attachment at various sites on the endotoxin. In a preferred embodinent, the type of label used in the presently claimed invention must generate a signal at the surface of an optical waveguide. Examples include fluorophores, colorimetric dyes, metal chelates or carbonyls, electrochemiluminescent labels, or luminescent labels. A label is selected so that a signal characteristic of a labelled endotoxin molecule when the labelled endotoxin molecule is bound to an endotoxin capture molecule, forming an endotoxin capture molecule-labelled endotoxin molecule (ECM-LEM) complex, can be detected in both the presence and absence of a competing endotoxin capture molecule--unlabelled analyte endotoxin molecule (ECM-AEM) complex.

The immobilization of the ECM can be via covalent or noncovalent chemistries. The objective is to affix the ECM to a substrate surface in such a way that the capture molecule retains its biological activity while remaining fixed to the substrate surface for the purpose of quantitation. For example, immobilization of an exemplary endotoxin capture molecule (ECM) may be carried out upon the surface of the exemplary substrate having a surface coated with an exemplary heterobifunctional crosslinking agent. For example, polymyxin B may be immobilized onto the exemplary substrate (having a surface coated with an exemplary heterobifunctional crosslinking agent) at a concentration of about 1–10 mg/ml of polymyxin B in an exemplary 0.1M NaBorate solution at an exemplary pH of 9.0. The prepared exemplary substrate is suspended in the polymyxin B solution for about 30 min. The pH of the exemplary solution is then neutralized using HCI. The exemplary substrate is then washed several times with PBS to remove any unreacted exemplary polymyxin B and to further neutralize the exemplary substrate surface.

Once the exemplary substrate has an exemplary capture molecule immobilized upon its surface, the process of the presently claimed competitive assay is carried out. The process of the presently claimed invention comprises:

(1) immobilizing one or more ECM upon a substrate;

(2) introducing at time $=t_0$, a standard sample of one or more labelled endotoxin molecules and an analyte sample containing or suspected of containing one or more analyte endotoxin molecules over the one or more immobilized ECMs to form one or more ECM-LEM complexes and, if any analyte endotoxin molecules are present in the analyte sample, to form one or more endotoxin capture molecule--analyte endotoxin molecule (ECM-AEM) complexes;

(3) measuring at time $=t_1$ the amount of one or more ECM-LEM complexes formed wherein $t_4 <(t_1 - t_0) <t_3$ minutes wherein $t_4$ is a time $=t_4$ I $t_3$ is a time $=t_3$, wherein $t_4$ is about 0.05 to about 0.20 minutes and $t_3$ is a time selected from the group consisting of about 10 minutes, 5 minutes, 4 minutes, 3 minutes, 2 minutes, 1 minute, 0.5 minute and 0.25 minute, respectively; and (4) calculating the amount, if any, of the ECM-AEM complexes formed.

The formation of the ECM-AEM complexes at the surface of a waveguide is measured using the waveguide to collect the signal generated by the label. The signal can be a change in refractive index, a phase shift in the light, fluorescence, luminescence, absorbance, respectively. Depending upon the type of signal generated, various means of quantitating the signal known in the art may be used. The device may or may not need a light source to excite the label. If needed, the excitation light can travel down the waveguide or excite the light from outside the waveguide.

Having described the invention, the following examples are given to illustrate specific applications of the invention, including the best mode now known to perform the invention. These specific examples are not intended to limit the scope of the invention described in this application.

EXAMPLES

Fluorimeter and Waveguide Configuration used for Examples

The fluorimeter and waveguides used in the examples described here were laboratory prototypes. A similar fluorimeter operating at 635 nm is commercially available (Research International, Woodinville, WA). Exemplary suitable dyes for use in conjunction with fluorimeter from Research International are the sulfoindocyanine dyes (cyanine based dyes e.g. Cy5 dyes) described by Mujumdar et. al. in the paper entitled Cyanine Dye Labeling Reagents: Sulfoindocyanine Succinimidyl Esters, BIOCONJUGATE CHEMISTRY, Vol. 4, No. 2, pp105–111 (March/April 1993) —incorporated herein by reference in its entirety and for all purposes, the dyes being available from Biological Detection Systems, Inc. located in Pittsburgh, Pennsylvania. For details of the device and waveguide construction, see L.C. Shriver-Lake, G.P. Anderson, J.P. Golden and F.S. Ligler, The effect of Tapering the Optical Fiber on Evanescent Wave Measurements 25 ANALYTICAL LETTERS 7, pp. 1183–1199 (1992), incorporated by reference herein in its entirety and for all purposes. See J.P. Golden, L.C. Shriver-Lake, G.P. Anderson, R.B. Thompson and F.S. Ligler, Fluorometer and Tapered Fiber Optic Probe for Sensing in the Evanescent Wave 31 OPTiCAL ENGINEERING No. 7, pp. 1458–1462 (July 1992), incorporated by reference herein in its entirety and for all purposes. See G.P. Anderson, J.P. Golden and F.S. Ligler, A Fiber Optic Biosensor: Combination Tapered Fibers Designed for Improved Signal Acquisition, 8 BIOSENSORS & BIOELECTRONICS, pp. 249–256 (1993), incorporated by reference herein in its entirety and for all purposes.

The detection optics in the fluorimeter used in these experiments were encased in a light-proof metal enclosure to reduce the effects of ambient light and electromagnetic influence on the detector circuitry. Key components include optics for launching and collecting the light mounted on kinematic mounts. A laser light source was selected for its moderate power, stability, narrow excitation bandwidth and efficient light coupling into the fiber. The exemplary rhodamine-based fluorescent labels (e.g. TRITC) used with the sensor in the examples described here were excited at 514 nm and emit in the 570 (+50 nm) nm range where there is little intrinsic fluorescence in most clinical and environmental samples. A 514 nm laser beam from an air-cooled 50-mW argon ion laser (Omnichrome 532, Chino, California) was launched into the most proximal end of the cladded fiber. The laser was adjusted to a 12-mW output to minimize bleaching of the fluorophores bound to the distal end of the optical fiber . The line filter (Melles Griot) removed plasma lines from the laser source. The laser beam passed through a chopper, a dichroic mirror and a spherical lens (f/i, one inch focal length bioconvex lens; Newport Corporation) onto the proximal end of the optical fiber. Approximately, 8 degrees of the fiber's numerical aperture of 23 degrees were filled. The collected fluorescence signal from the distal end of the optical fiber traveled the reverse path to the dichroic mirror where it was reflected through a longpass filter (KV550) onto a silicon photodiode. The chopper and photodiode (EG&G Judson) were connected to a lock-in amplifier (LIA, Stanford Research Systems, Sunnyvale, Calif.) and computer for phase sensitive detection via chopper controller. The photodiode was selected rather than a photomultiplier tube because of low cost, reliability and compatibility with the lock-in amplifier. The data, measured as pV, were collected using the laptop computer.

The fiber optic waveguide used in the examples was made from a length of step-index plastic clad silica optical fiber (200 um diameter core, Quartz et Silice, Quartz Products, Tuckerton, Delaware) with a connector on the proximal end to facilitate replacement and alignment. The distal end was modified to perform biochemical assays in the evanescent wave. At the distal end of the fiber, 12.5 cm of cladding was stripped away from the core by removal of the buffer and cladding with a razor blade. Residual cladding was removed by immersing this end of the optical fiber in concentrated hydrofluoric acid (HF) for 1 minute. This distal end portion of the fiber was the sensing region on which the capture molecules were immobilized. The combination taper probe (i.e. the combination of a first short tapered section and a second longer, shallower tapered section) was prepared by slowly immersing the declad distal end of the fiber into concentrated HF, using a computer controlled stepper motor. Two to three centimeters of the distal, unclad end of the fiber was first lowered into the concentrated HF acid. The distal, unclad end of the fiber was further lowered at a constant rate of about 0.53 cm/minute for the next 9 cm to create the gradually tapered section . The distal, unclad fiber was even further lowered into the concentrated HF acid for another 1 cm at a constant rate of about 0.045 cm/minute to create the more steeply tapered section. This relatively steep tapered section was tapered from the original 100 ,m radius down to 63 am. The taper dimensions were measured with a calibrated optical microscope. See G.P. Anderson, J.P. Golden and F.S. Ligler, A Fiber Optic Biosensor: Combination Tapered Fibers Designed for Improved Signal Acquisition, 8 BIOSENSORS & BIOELECTRONICS, pp. 250–251 and FIG. 1 at pp. 250 (1993), incorporated by reference herein in its entirety and for all purposes.

For immobilization of the capture molecules, the distal unclad tapered fiber having surface hydroxyl groups was immersed in a 2% solution of mercaptopropyltrimethoxysilane (MTS) dissolved in toluene for 30 minutes under $N_2$. Thereafter, the fiber was rinsed with toluene also under $N_2$. The silanized fiber was then 5 placed in a 2 mM solution of a heterobifunctional crosslinking agent, y-maleimidobutyryloxy succinimide ester, for 1 h. The fiber was then rinsed in phosphate buffered saline (PBS) at pH 7.4. Lastly, the distal end of the fiber is suspended in a solution of 0.05 mg/ml of lectin, 0.05mg/ml solution of IgG antibody for endotoxin, 0.02 mg/ml of endotoxin neutralizing protein (ENP), 0.01,g/ml of polymyxin B, 0.1,ag/ml of polymyxin B, 1.0mg/ml of polymyxin B, or 10.0mg/ml of polymyxin B, respectively, for 2 h. The fibers with immobilized capture molecules are stored in endotoxin-free PBS at 4° C. See Bhatia et al., Analvtical Biochemistrv, 178, 408–413 (1989), incorporated herein by reference in its entirety and for all purposes.

After the immobilization of the capture molecules, the entire uncladded portion of the exemplary combination tapered fiber optic waveguide was sealed into a flow chamber constructed from an exemplary shortened 200 ,l capillary tube and tee connectors, having a total length of 12 –13 cm. The distal end of the fiber was glued outside the chamber, allowing only light from the evanescent wave to enter the fiber surrounded by the solution within the tee connection capillary. Both ends of the capillary tube were sealed with hot-melt glue, with the clad region of the fiber extending into the proximal portion of the apparatus. The sample to be tested was introduced over the distal end of the optical fiber via sample inlet and exited at sample outlet. Use of this capillary tube apparatus allows one to test a given analyte sample solution over the optical waveguide and to wash the waveguide before introducing another analyte sample solution.

Example 1

Labelled endotoxin was prepared and the binding of the labelled endotoxin to the capture molecule immobilized on the waveguide was measured. In this example, polymyxin B was immobilized on the fiber using a solution of 10mg/ml polymyxin B as described above.

A standard sample of labelled endotoxin molecules was made according to the following procedure. A known amount of endotoxin (for example, 1 mg/ml) was dissolved in 5.0 ml of a 0.1M NaBorate solution at pH 10.5 and vortexed vigorously for at least 15 minutes at room temperature. A fluorescent label, tetramethyl isothiocyanate (TRITC, Sigma), was added to the vortexed solution to a w/w concentration of 1:100 of endotoxin:TRITC. The TRITC/endotoxin sample was incubated at 37 ° C. in the dark for 4 h with intermittent vortexing . The TRITC labelled endotoxin was dialyzed against several changes of 0.15 M NaCl. Any unbound TRITC was removed by passing the endotoxin solution over a Sephadex G-25 column (Sigma). The standard sample of labelled endotoxin was collected in fractions and the ratio of endotoxin to TRITC calculated. Molar ratios of fluorophore to endotoxin of approximately 0.8:1 to about 1.5:1 (i.e. molar conc. of fluorophore : molar conc. of endotoxin) were considered acceptable for use in this example. There were two different endotoxins used, the E.Coli EH 100 Ra mutant endotoxin (lacking the 0-antigenic region) and from E.Coli 0128:B12 endotoxin, respectively.

The TRITC labelled standard sample of endotoxin was further used according to the following procedure. Labelled endotoxin was reconstituted in PBS which contained either 2 mg/ml of bovine serum albumin (BSA) or 0.1 % Triton X-114. The labelled endotoxin standard sample was introduced through the capillary tube containing the fiber optic probe coated with the immobilized capture molecule. Binding was observed from about 0–2 minutes at 30 second intervals. The excitation laser beam (514nm) was blocked between evanescent wave signal measurements to avoid photobleaching.

Figure 1:
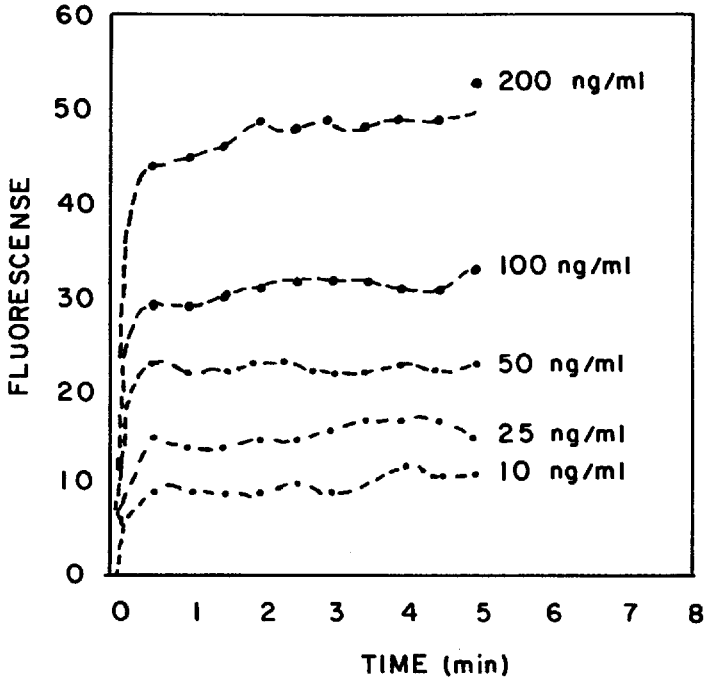
FIG. 1 is a concentration-response curve obtained from the direct binding of increasing concentrations of fluorescently labelled *E. coli* 0128:B12-endotoxin to a capture molecule, polymyxin B, the capture molecule being covalently bound to the surface of a combination tapered fiber optic waveguide probe.

FIG. 1 depicts response curves obtained from the direct binding of increasing concentrations of fluorescently labelled *E. coli* 0128:B12 endotoxin to a capture molecule, polymyxin B, the capture molecule being covalently bound to the surface of a fiber optic waveguide. Note that the fluorescent label used is tetramethyl rhodamine-5-isothiocyanate (TRITC). The labelled endotoxin standard was introduced through the capillary tube containing the fiber optic waveguide coated with the immobilized capture molecule. Binding signals were measured at 30 second intervals. The excitation laser beam (514 nm) was blocked between signal measurements to avoid photobleaching. The signal measured from the standard solutions of labelled endotoxin was determined using a different fiber waveguide for each recording. The response is measured in microvolts ($\mu$Volts) which response varies proportionately with the concentration of endotoxin present in the sample tested. The curves plot the change in fluorescence at the waveguide surface as a function of the concentration of fluorescently labelled *E. coli* 0128:B12-endotoxin in solution.

Example 2

In order (a) to demonstrate the binding of labelled endotoxin by a different capture molecule and (b) to demonstrate the quantitation of signal produced by increasing concentrations of the labelled endotoxin, waveguides coated with anti-endotoxin antibody were exposed to increasing concentrations of labelled endotoxin.

Figure 2:
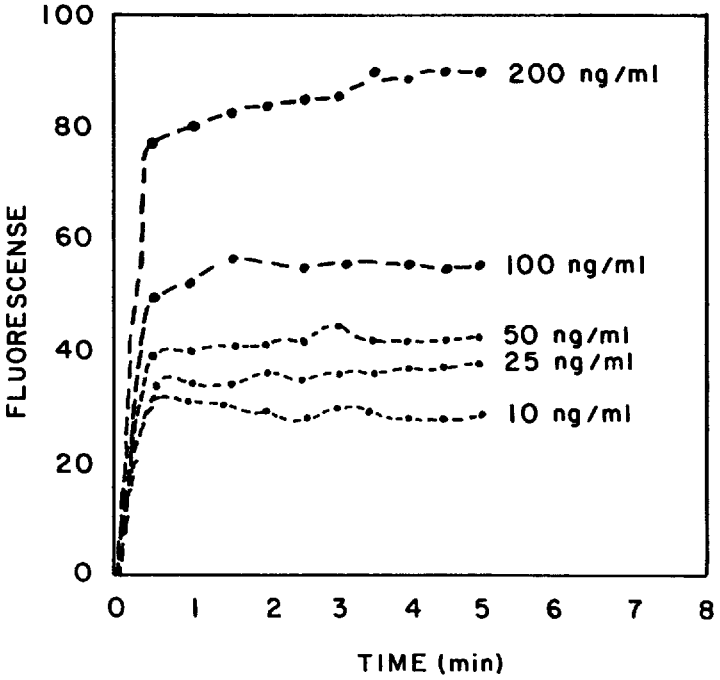
FIG. 2 is a concentration-response curve obtained from the binding of increasing concentrations of fluorescently labelled *E. coli* 0128:B12-endotoxin to a capture molecule, goat IgG, the capture molecule being covalently bound to the surface of a combination tapered fiber optic waveguide probe.

FIG. 2 is a concentration-response curve obtained from the binding of increasing concentrations of fluorescently labelled *E. coli* 0128:B12-endotoxin to a capture molecule, goat IgG antibody specific for *E. coli* 0128:B12 endotoxin, the capture molecule being covalently bound to the surface of a fiber optic waveguide. Note that the fluorescent label used is tetramethyl rhodamine-5-isothiocyanate (TRITC). The response is measured in microvolts ($\mu$Volts) which response varies proportionately with the concentration of endotoxin present in the sample tested. The curve is a plot of change in fluorescence as a function of the concentration of fluorescently labelled *E. coli* 0128:B12 endotoxin in PBS +2 mg/ml BSA. The complex of antibody-endotoxin-TRITC was detected as it formed at the waveguide surface.

Example 3

Figure 3:
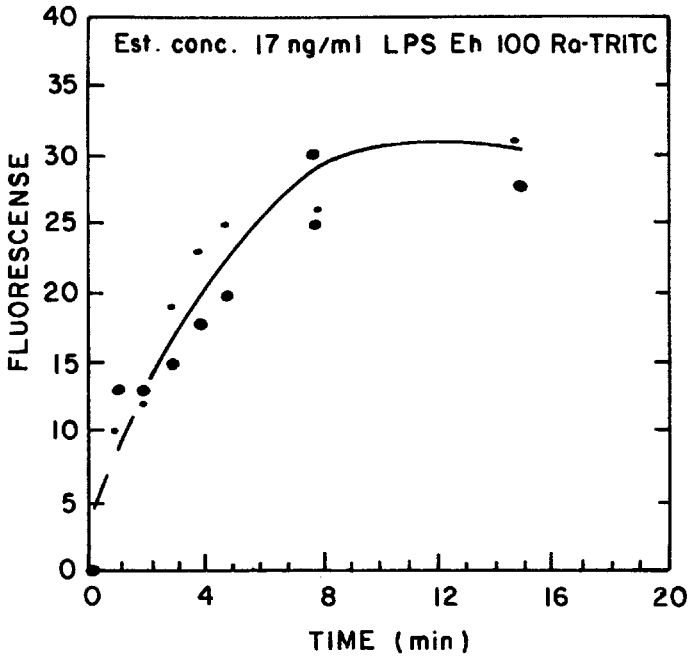
FIG. 3 is a concentration-response curve obtained from the binding of 17ng/ml of fluorescently labelled *E. coli* EH100 Ra mutant endotoxin to a capture molecule, limulin lectin, the capture molecule being immobilized on to the surface of a combination tapered fiber optic waveguide probe. The response is measured in microvolts ($\mu$Volts).

In order to demonstrate the binding of labelled endotoxin to yet another capture molecule on the surface of the waveguide, the waveguide was coated with limulin lection. FIG. 3 is a time-response curve obtained from the binding of 17 ng/ml of fluorescently labelled *E. coli* EhlOO Ra mutant endotoxin to a capture molecule, limulin lectin, the capture molecule being immobilized on to the surface of a fiber optic waveguide. The response is measured in microvolts ($\mu$Volts). The complex of limulin lectin-endotoxin-TRITC was detected as it formed at the surface of the waveguide and within 1 minute of after the addition of the TRITC labelled endotoxin.

Example 4

In order to demonstrate a quantitative dose-response relationship between the concentration of labelled endotoxin put over the waveguide and the signal produced, waveguides were coated with polymxyin B as the capture molecule. FIG. 4 is a concentration-response curve obtained from the binding of increasing concentrations of fluorescently labelled *E. coli* 0128:B12 endotoxin to a capture molecule, polymyxin B, the capture molecule being immobilized on to the surface of a combination tapered fiber optic waveguide probe. The response is measured in microvolts ($\mu$Volts) which response varies proportionately with the concentration of endotoxin present in the sample tested. Under the conditions of the assay used to obtain FIG. 4, the capture molecule, polymyxin B, was immobilized onto the surface of a fiber optic waveguide probe and the assay was conducted in PBS +2 mg/ml BSA. The complex of polymyxin B-endotoxin-TRITC was detected as it formed at the surface of the waveguide. The response shows percent signal (compared to the signal produced on each fiber for 500 ng/ml of TRITC-endotoxin) as a function of increasing concentrations of fluorescently labelled endotoxin from 12.5 ng/ml to 500 ng/ml.

Example 5

Once the signal measured from the standard solution of labelled endotoxin was determined, the change in signal caused by a competitive binding of unlabelled endotoxin and the standard endotoxin solution was measured. Note that the subsequent signal was produced by a comingled solution of the standard sample of labelled endotoxin and the analyte sample of the unlabelled endotoxin flowing concomittantly over the fiber optic probe held within the capillary tube, the probe being prepared using polymxyxin B at 10 ng/ml.

FIG. 5 is a concentration-response curve obtained from the competitive binding of increasing concentrations of unlabelled *E. coli* 0128:B12 endotoxin in the presence of fluorescently labelled *E. coli* 0128:B12 endotoxin. The fluorescently labelled and unlabelled endotoxin were dissolved in PBS +2 mg/ml BSA. The fluorescent label used was TRITC. Increasing concentrations of unlabelled endotoxin (0–250 ng/ml) were added to a standard concentration of TRITC-endotoxin of 200 ng/ml. The response is measured in microvolts ($\mu$Volts) and each point is an average of triplicate determinations and each point is standardized to % inhibition of signal from a 100% response (100% response is wherein no unlabelled endotoxin is present in solution and 200 ng/ml of TRITC-endotoxin is present in solution of PBS +2 mg/ml BSA). Under the conditions of the competitive assay used to obtain FIG. 5, the capture molecule, polymyxin B, was immobilized onto the surface of a fiber optic waveguide probe and the assay was conducted in PBS +2 mg/ml BSA. The complex of polymyxin B-endotoxin-TRITC was detected at the surface of the fiber optic waveguide. The response is standardized to show % inhibition of signal as a function of increasing concentrations of unlabelled endotoxin from 0 to 250 ng/ml. Note that 10% of the expected fluorescent signal (i.e. 100% response, supra) is inhibited at a concentration of 12.5 ng/ml of unlabelled endotoxin in solution.

Example 6

The affect of serum on endotoxin binding and on the competitive assay for endotoxin was determined according to the following procedure.

A concentration response curve obtained from the binding of increasing concentrations of fluorescently labelled *E. coli* 0128:B12 endotoxin to a capture molecule, polymyxin B, the capture molecule being immobilized on to the surface of a combination tapered fiber optic waveguide probe is depicted in FIG. 6. The response is measured in microvolts ($\mu$Volts) which response varies proportionately with the concentration of endotoxin present in the sample tested and each point is the mean ± standard error of triplicate determinations. Under the conditions of the assay used to obtain FIG. 6, the capture molecule, polymyxin B, was immobilized onto the surface of a fiber optic waveguide probe and the assay was conducted in PBS +2 mg/ml BSA containing 0% serum, 1% serum, 5% serum, or 20% serum. The complex of polymyxin B-endotoxin-TRITC was detected at the surface of the fiber optic waveguide. The figure shows the percent signal as a function of increasing concentrations of fluorescently labelled endotoxin from 12.5 ng/ml to 500 ng/ml. Note that 25 ng/ml of endotoxin-TRITC can be detected in 20% serum and 12.5 ng/ml was detected in 1% serum.

Example 7

FIG. 7 is a concentration-response curve obtained from the competitive binding of increasing concentrations of unlabelled *E. coli* 0128:B12 endotoxin in the presence of fluorescently labelled *E. coli* 0128:B12 endotoxin. The fluorescently labelled and unlabelled endotoxin were dissolved in PBS +2 mg/ml BSA containing 0% serum, 1% serum, 5% serum or 20% serum, respectively. The fluorescent label used was TRITC. Increasing concentrations of unlabelled endotoxin (0–250ng/ml) were added to a standard concentration of TRITC-endotoxin at a concentration of 200 ng/ml. The response is measured in microvolts ($\mu$Volts) and each point is an average of triplicate determinations and each point is standardized to percent inhibition of signal from a 100% response (100% response is wherein no unlabelled endotoxin is present in solution and 200 ng/ml of TRITC-endotoxin is present in solution of PBS +2 mg/ml BSA). Under the conditions of the competitive assay used to obtain FIG. 7, the capture molecule, polymyxin B, was immobilized onto the surface of a fiber optic waveguide and the assay was conducted in PBS +2 mg/ml BSA. The complex of polymyxin B-endotoxin-TRITC was detected as it formed at the waveguide surface. The response is standardized to show percent inhibition of signal as a function of increasing concentrations of unlabelled endotoxin from 0 to 250 ng/ml. The curve for 0% serum (not shown) was identical to that for 1% serum. Note the expected fluorescent signal (i.e. as compared to 100% response, supra) is inhibited at a concentration of 25 ng/ml of unlabelled endotoxin in solution.

What is claimed is:

1. A process for detecting endotoxin in a concentration by a competitive assay, said process comprising the steps of:

(1) immobilizing polymyxin B upon a substrate under a phosphate-buffered saline solutions;

(2) introducing at time $=t_0$, a standard sample of one or more labelled endotoxin molecules labelled with TRITC (LEM) and an analyte sample containing or suspected of containing one or more analyte endotoxin molecules over said one or more immobilized polymyxin B to form one or more polymyxin B—LEM complexes and, if any analyte endotoxin molecules are present in the analyte sample, to form one or more polymyxin B—analyte endotoxin molecule complexes in phosphate-buffered saline;

(3) measuring at time $=t_1$ the amount of one or more polymyxin B—LEM complexes formed wherein $t_4 \leqq (t_1-T_0) \leqq t_3$ minutes, wherein $t_3$ is a time $=t_3$ and wherein $t_4$ is a time $=t_4$; and (4) calculating the amount, if any, of the polymyxn B—analyte endotoxin molecule complexes formed.

2. The method of claim 1, wherein said substrate is an optical fiber.

* * * * *